US006462180B1

(12) United States Patent
Lebing et al.

(10) Patent No.: US 6,462,180 B1
(45) Date of Patent: Oct. 8, 2002

(54) METHOD OF PREPARING α-1 PROTEINASE INHIBITOR

(75) Inventors: Wytold Lebing, Clayton; Mark D. Chavez, Raleigh; David W. Ownby, Clayton; Susan Trukawinski, Cary; Woody D. Wood, Selma, all of NC (US)

(73) Assignee: Bayer Corporation, Pittsburgh, PA (US)

( * ) Notice: Subject to any disclaimer, the term of this patent is extended or adjusted under 35 U.S.C. 154(b) by 0 days.

(21) Appl. No.: 09/449,695

(22) Filed: Nov. 24, 1999

(51) Int. Cl.$^7$ .......................... C07K 17/00; C07K 1/00; A61K 38/04; A23J 1/00
(52) U.S. Cl. ...................... 530/395; 530/329; 530/416; 530/831
(58) Field of Search ................................ 530/395, 416, 530/329, 831; 260/112

(56) References Cited

U.S. PATENT DOCUMENTS

| | | | |
|---|---|---|---|
| 3,293,236 A | 12/1966 | Schultze et al. | 260/112 |
| 4,379,087 A | 4/1983 | Coan et al. | 260/112 B |
| 4,439,358 A * | 3/1984 | Coan et al. | 260/112 |
| 4,496,689 A | 1/1985 | Mitra | 525/541 |
| 4,629,567 A | 12/1986 | Bollen et al. | 210/635 |
| 4,656,254 A | 4/1987 | Shearer et al. | 530/393 |
| 4,697,003 A | 9/1987 | Coan | 530/380 |
| 5,319,072 A | 6/1994 | Uemura et al. | 530/393 |
| 5,610,285 A * | 3/1997 | Lebing et al. | 530/416 |
| 5,616,693 A | 4/1997 | Hwang et al. | 530/392 |
| 5,831,003 A * | 11/1998 | Baumbach et al. | 530/329 |

FOREIGN PATENT DOCUMENTS

| | | |
|---|---|---|
| WO | WO 95/35306 | 12/1995 |
| WO | WO 97/09350 | 3/1997 |

OTHER PUBLICATIONS

Chen, S. X., Hammond, D. J., Klos, A. M., Wood, W. D., Wydick, J. E., and Lebing, W. R., "Chromatographic purification of human $α_1$ proteinase inhibitor from dissolved Cohn fraction IV–1 paste", J. Chromatography A, 800:207–218 (1998).

Chen, S. X., Hammond, D. J., Lang, J. M., Lebing, W. R., "Purification of $α_1$ Proteinase Inhibitor from Human Plasma Fraction IV–1 by Ion Exhange Chromatography", Vox Sang, 74:232–241 (1998).

Coan, M. H., Brockway, W. J., Eguizabal, H., Krieg, T., and Fournel, M., "Preparation and Properties of Alpha$_1$–Proteinase Inhibitor Concentrate from Human Plasma", Vox Sang, 48: 333–342 (1985).

Hein, R. H., Van Beveren, S. M., Shearer, M. A., Coan, M. H., and Brockway, W. J., Production of alpha$_1$–proteinase inhibitor (human), Eur. Respir. J., 3(9): 16s–20s (1990).

* cited by examiner

Primary Examiner—Christopher R. Tate
Assistant Examiner—Randall Winston
(74) Attorney, Agent, or Firm—Womble Carlyle Sandridge & Rice, PLLC; Carl B. Massey, Jr.

(57) ABSTRACT

Purification of α-1 proteinase inhibitor (α-1 PI) from aqueous solutions, such as human plasma, is accomplished by precipitation of contaminating proteins from the aqueous solution, followed by dilution of the solution to adjust its conductivity, and passing of the solution through an anion exchange resin. The conductivity of the solution is adjusted so that the α-1 PI binds to the anion exchange resin, while other contaminating proteins and solvent pass through the resin. Further purification may be accomplished by cation chromatography, which takes advantage of the fact that α-1 PI does not bind to the cation column under certain conditions. Some embodiments of the invention also include virus removal and/or inactivation by methods such as nanofiltration and such as contact with a non-ionic detergent. The methods of the present invention result in greater yield, purity, and pathogenic clearance of plasma fractions than known methods.

33 Claims, No Drawings

METHOD OF PREPARING α-1 PROTEINASE INHIBITOR

FIELD OF THE INVENTION

The invention relates to the purification of alpha-1 proteinase inhibitor (α-1 PI) from aqueous solutions. More specifically, the invention relates to the purification of α-1 PI from blood plasma or from plasma fractions produced from Cohn-Oncley fractionation with chromatography. Viral removal is accomplished by the addition of PEG and by nanofiltration. Inactivation of enveloped viruses is accomplished by addition of detergent prior to the chromatography process.

BACKGROUND

Alpha-1 proteinase inhibitor (α-1 PI) is a glycoprotein with a molecular weight of about 55,000 Daltons. The protein is a single polypeptide chain to which several oligosaccharide units are covalently bound. Alpha-1 PI acts as an inhibitor of endogenous proteases, such as trypsin, chymotrypsin, pancreatic elastase, skin collagenase, renin, urokinase and proteases of polymorphonuclear lymphocytes.

Alpha-1 PI is currently used therapeutically to treat persons having a genetically caused deficiency of α-1 PI. In such a condition, α-1 PI is administered to inhibit lymphocyte elastase in the lungs. Lymphocyte elastase breaks down foreign proteins in the lungs. When α-1 PI is not present in sufficient quantities to regulate elastase activity, the elastase breaks down lung tissue. In time, this imbalance results in chronic lung tissue damage and emphysema. Alpha-1 PI has been successfully used to treat this form of emphysema.

The demand for α-1 PI typically exceeds the available supply. Alpha-1 PI for therapeutic use is currently purified from human plasma. This source of the protein is limited, which contributes to the low supply. In order to maximize the available supply of α-1 PI, a process for purifying α-1 PI from human plasma should have the highest possible yield. The purity of the α-1 PI isolated from human plasma is also critical, because trace impurities can stimulate immune responses in patients who are receiving α-1 PI. Finally, the process of purifying α-1 PI from human plasma using current techniques requires an extensive amount of time, for the separation of the α-1 PI from other proteins, viruses, etc. All of these factors (i.e., low yields, long production times, and low purity), contribute to the inadequate supply of α-1 PI.

Various methods of purifying α-1 PI from human plasma have been described. Bollen, et al., U.S. Pat. No. 4,629,567 (1986) used five different chromatography steps to purify the α-1 PI from yeast, E. coli, and human plasma. The five steps involved DEAE ion exchange, thiol-disulfide exchange, heparin affinity, zinc-chelate chromatography, and amino hexyl ion exchange. No purity and yield data were shown.

Novika, et al., Gematol. Transfuziol. 34:46–50 (1989) reported isolation methods from the by-products of the manufacture of blood products. They used affinity, DEAE cellulose, and gel filtration chromatographies. The purity and yield data were not available.

Podiarene, et al., Vopr. Med. Khim. 35:96–99 (1989) reported a single step procedure for isolation of α-1 PI from human plasma using affinity chromatography with monoclonal antibodies. Alpha-1 PI activity was increased 61.1 fold with a yield of 20%.

Burnouf, et al., Vox. Sang. 52, 291–297 (1987) starting with plasma supernatant A (equivalent to Cohn Fraction II+III) used DEAE chromatography and size exclusion chromatography to produce an α-1 PI which was 80–90% pure (by SDS-PAGE) with a 36-fold increase in purity. Recovery was 65–70% from the supernatant A.

Hein, et al., Eur. Respir. J. 9:16s–20s (1990) and co-owned U.S. Pat. No. 4,697,003 present a process which employs Cohn Fraction IV-1 as the starting material and utilizes fractional precipitation of α-1 PI with polyethylene glycol followed by anion exchange chromatography on DEAE Sepharose®. The final product has a purity of about 60% with 45% yield.

Dubin, et al., Prep. Biochem. 20:63–70 (1990) have shown a two step chromatographic purification. First α-1 PI, CI inhibitor, α-1 antichymotrypsin, and inter α-1 trypsin inhibitor were eluted from Blue Sepharose® and then α-1 PI was purified by gel filtration. Purity and yield data were not available.

Ballieux, et al., purified an α-1 PI and proteinase-3 complex from purulent sputum using 4-phenylbutylamine affinity chromatography, cation exchange, and a final immunoaffinity step (Ballieux, B. E., et al., J. Immunol. Methods 159:63–70 (1993)). The pH of the buffer used in the cation exchange step was 7.0. Under the conditions used, most of the sputum proteins bound to the resin, but α-1 PI and proteinase-3 passed through without binding.

Jordan, et al., U.S. Pat. No. 4,749,783 (1988) described a method where biologically inactive proteins in a preparation were removed by affinity chromatography after a viral inactivation step. The basis of the separation between the native and denatured forms of the protein was the biological activity of the native protein towards the affinity resin and not physical differences between the native and denatured proteins.

Lebing and Chen, co-owned U.S. Pat. No. 5,610,285, described a method where α-1 PI was captured from IV-1 paste suspension using a DEAE chromatography step. The collected solution was ultrafiltered then applied to an S-cation column for initial purification. Alpha-1 PI was collected as the flow-through fraction. The product, in a sucrose solution, was then treated with TNBP/cholate in order to inactivate viruses. Following filtration and ultrafiltration, the product was applied to a second S-cation column for final purification. Once the product was formulated and freeze dried, it was virally inactivated a second time by heating to 80° C. for 72 hours. Product purity and virus safety were greatly improved versus the Hein process, described above, but, in practice, the Lebing and Chen process was too resource intensive for large-scale manufacturing.

A process for the purification of α-1 PI that improves the yield and purity of the α-1 PI, that requires a shorter production time and uses less resources (such as reagents, water, resins, and column size) is needed. The present invention provides a process of purifying α-1 PI from a blood plasma fraction with a higher yield, higher purity, shorter production time, and use of less resources than known methods.

SUMMARY OF THE INVENTION

The present invention provides methods for purifying α-1 PI from an aqueous solution containing α-1 PI. A portion of contaminating proteins is removed from the aqueous solution, so that a partially purified solution containing α-1 PI is obtained. The contaminating proteins may, for example, be precipitated by adding polyethylene glycol (PEG) to the aqueous solution and adjusting the pH of the solution to from about 5.0 to about 6.0. The conductivity of the partially purified solution is then adjusted, such as by diluting it to reduce its conductivity, for example. The purified solution is diluted with water, for example, and the water may contain sodium phosphate. The conductivity of the solution is adjusted so that α-1 PI will bind to an anion exchange resin. This conductivity is typically between about 2.0 milliSiemens (mS) and about 6.0 mS, for example. The method further includes passing the purified solution over an anion exchange resin so that the α-1 PI in the solution binds to the anion exchange resin. The α-1 PI can then be eluted from the anion exchange resin to obtain an eluted solution containing α-1 PI.

In another embodiment of the invention, a portion of contaminating proteins is removed by washing the anion exchange resin, to which α-1 PI is bound, with a buffer solution. The buffer solution removes a portion of contaminating proteins that are bound to the anion exchange resin without removing α-1 PI bound to the anion exchange resin.

In another embodiment of the invention, viruses are deactivated prior to dilution of the purified solution and its addition to an anion exchange resin. The viral inactivation occurs by, for example, adding a detergent to the purified solution to obtain a mixture of purified solution and detergent and adjusting the pH of the mixture to from about 6.5 to about 8.5. The detergent is preferably a non-ionic detergent, such as Tween 20, for example.

In a further embodiment, the method of the invention also includes a viral removal step. The viral removal step occurs by filtration of the diluted, purified solution, such as, for example, by nanofiltration.

In another embodiment, the method further includes passing the eluted solution obtained from the anion exchange resin through a cation exchange resin. The pH, conductivity, and protein concentration of the eluted solution are adjusted so that α-1 PI will not bind to the cation exchange resin. The solution is then passed over the cation exchange resin, and a flowthrough that contains α-1 PI is collected.

In other embodiments of the invention, α-1 PI is purified from Fraction IV-1 of the Cohn-Oncley fractionation procedure. The Cohn Fraction IV-1 may be suspended in an aqueous solution for purposes of the purification process. An embodiment of the invention provides for removing a portion of contaminating proteins from a Cohn Fraction IV-1 to obtain a purified solution containing α-1 PI, adjusting the conductivity of the purified solution so that α-1 PI will not bind to an anion exchange resin, passing the purified solution through a n anion exchange resin, and eluting α-1 PI from the anion exchange resin to obtain an eluted solution containing α-1 PI.

Methods of the present invention provide for the isolation of α-1 PI from aqueous solutions, such as human plasma, at yield and purity levels far above known processes. The methods of the present invention provide for a yield that is 50% greater than yields obtained with current production procedures and provides α-1 PI at a purity that is increased to greater than 95%. The methods of the invention can produce a yield of α-1 PI of at least 75% from Cohn Fraction IV-1 starting material. Methods of the invention can produce α-1 PI having a purity of at least 98% by imimunonephelometry. Finally, methods of the invention also reduce the production time for the purification of α-1 PI by approximately 40 hours to a production time no longer than 40 hours. These and other aspects of the invention will be made more apparent from the following description and claims.

DETAILED DESCRIPTION

The present invention provides a process for purifying α-1 PI from an aqueous solution containing α-1 PI, such as human plasma, for example. In methods of the invention, contaminating proteins are removed from the aqueous solution before it is passed through an anion exchange resin. Prior to passing the solution through the anion exchange resin, the conductivity of the solution is adjusted, preferably by diluting the solution, so that the α-1 PI will bind to the anion exchange resin. This typically occurs at a conductivity of between about 2.0 mS and about 6.0 mS. The α-1 PI is then selectively eluted from the anion exchange resin to provide α-1 PI at yield and purity levels above those obtained with current processes.

A known procedure for the purification of α-1 PI begins with Fraction IV-1 paste, as obtained through the Cohn-Oncley fractionation procedure for human plasma. See, e.g., E. J. Cohn, et al., *J. Amer. Chem. Soc.*, 68, 459 (1946); E. J. Cohn, U.S. Pat. No. 2,390,074; and Oncley, et al., *J. Amer. Chem. Soc.*, 71, 541 (1949) the entire disclosures of which are hereby incorporated by reference herein. The Cohn-Oncley process involves a series of cold ethanol precipitation steps during which specific proteins are separated according to isoelectric point by adjusting pH, ionic strength, protein concentration, temperature and ethanol concentration. The Fraction IV-1 paste obtained by this procedure is dissolved in a buffer solution and heated to activate α-1 PI. An initial purification step includes the precipitation of contaminating proteins and lipids from the dissolved Fraction IV-1. The α-1 PI is then precipitated from the dissolved Fraction IV-1 solution, and the crude α-1 PI is passed through an anion exchange resin to remove contaminating proteins. A viral inactivation is accomplished by pasteurization for 10 hours at 60° C. in a sucrose solution. Following pasteurization, the α-1 PI is diafiltered, bulked in NaCl/Na$_3$PO$_4$, sterile filtered, and lyophilized.

In a preferred embodiment of the invention, the starting material for the process is Cohn Fraction IV-1, although other fractions, such as Cohn Fraction II+III, for example, can be used as a starting material. This fraction may be dissolved in an aqueous solution, such as a tris-(hydroxymethyl)amino methane (Tris) buffer solution, for example. Fraction IV-1 is typically a paste that can be dissolved in Tris buffer at a pH of about 9.25 to about 9.5 at about 40° C. A salt, such as sodium chloride (NaCl) may also be added to the solution.

The process of the invention includes the removal of at least a portion of contaminating proteins from the aqueous solution to obtain a purified solution that contains α-1 PI. Such contaminating proteins may include fibrinogen and albumin, for example. The portion of contaminating proteins is preferably removed by precipitation with a polyalkylene glycol, such as polyethylene glycol (PEG) or polypropylene glycol (PPG), for example. Other alcohols that are known to those of skill in the art to have similar properties may be used. PEG, the preferred polyalkylene glycol for use in methods of the invention, has a molecular weight of between about 2,000 and about 10,000, and preferably has a molecular weight of between about 3,000 and about 4,000. The PEG added to the solution is at least about 2% weight per volume of the mixture formed, is preferably about 3% to 15%, and is most preferably 11.5%. The pH of the solution may also be adjusted to precipitate the contaminating proteins. The pH is typically adjusted to between about 5.0 and about 6.0. The pH of the solution is adjusted by addition of an acid, such as acetic acid. The precipitate may then be separated from the solution by filtration, centrifugation, or any other conventional means known in the art, to obtain a filtrate containing α-1 PI.

The conductivity of the filtrate is then adjusted prior to passing the filtrate over an anion exchange resin. The equilibrium between an ion exchange resin and a protein solution is influenced by the ionic strength of the solution (see, e.g., Yamamato, et al., *Biotechnol. Bioeng.*, 25:1373–91 (1983)). The conductivity of the filtrate is therefore adjusted so that the α-1 PI in the filtrate will bind to an anion exchange resin. This conductivity is typically between about 2.0 mS and 6.0 mS when measured at 25° C., but other ranges of conductivity may be necessary to bind the α-1 PI to an anion exchange resin. The conductivity is preferably adjusted by dilution of the filtrate, and not by gel filtration, diafiltration, or other means of salt removal. The filtrate is preferably diluted with water, which may contain sodium phosphate ($Na_3PO_4$), or other buffers capable of providing a pH of about 6–7.

After dilution of the filtrate, the solution is applied directly to an anion exchange resin. Unlike known methods, as described above, the filtrate is not subjected to further PEG precipitation or diafiltration prior to chromatographic separation. The diluted filtrate is passed over an anion exchange resin, which is preferably a quaternary aminoethyl (QAE) resin. While QAE chromatography is preferred, other anion exchange resins, such as trimethylamino ethane (TMAE) and diethyl aminoethyl (DEAE), may be used in methods of the invention. The α-1 PI binds to the anion exchange resin. In a preferred embodiment, the anion exchange resin is washed with a buffer solution, such as an $Na_3PO_4$ buffer, to remove another portion of contaminating proteins. The proteins typically removed are albumin and transferrin. During the buffer wash, α-1 PI remains bound to the anion exchange resin. After the buffer wash, α-1 PI is eluted from the anion exchange resin to obtain an eluted solution containing purified α-1 PI. Ceruloplasmin remains bound to the column during both the wash and elution.

A further purification of the protein may be accomplished by passing the eluted solution containing the α-1 PI through a cation exchange resin. The pH, conductivity, and protein concentration of the eluted solution are adjusted so that α-1 PI does not bind to the cation exchange resin. The influences of pH, conductivity, and protein concentration on the binding of α-1 PI to a cation exchange resin are set forth in co-owned U.S. Pat. No. 5,610,825, the entire disclosure of which is hereby incorporated by reference herein.

Viral inactivation and/or viral removal also play a part in the purification of α-1 PI from aqueous solutions, such as human plasma, for example. Known processes for the purification of α-1 PI utilize a dry heat treatment for the inactivation of viruses. This treatment can denature α-1 PI protein, however, thereby reducing the yield and/or purity of the α-1 PI. The methods of the invention deactivate and remove viruses without this heat treatment step, thereby increasing both yield and purity of α-1 PI obtained.

The above-described precipitation of contaminating proteins with 11.5% PEG also serves as one of the virus removal steps. Precipitation with 11.5% PEG removes both enveloped and non-enveloped viruses from the blood plasma fraction. This precipitation removes, with a $\geq 4$ logs of clearance, at least four viruses, including HIV-1, BVDV, PRV, and Reovirus Type 3. In comparison, the dry heat process of known methods only results in $\geq 4$ logs of clearance of three of these viruses; the Reovirus Type 3 is only removed at 1 log clearance. Additionally, the 11.5% PEG precipitation step has been shown to result in $\geq 4$ logs of clearance of transmissible spongiform encephalopathies (i.e., TSE prions) from the blood plasma fraction. (See co-owned, co-pending application entitled *Method of Separating Prions from Biological Material*, filed on even-date herewith.)

Another viral deactivation is accomplished by addition of a non-ionic detergent to the aqueous solution. This step is preferably taken prior to passing the solution through the anion exchange resin. Non-ionic detergents for use in methods of the invention include, but are not limited to, Tweens, such as Tween 20 and Tween 80. Tween 20 is the preferred non-ionic detergent for use in methods of the invention. Tween 20 may be added at from about 0.33% to about 10% weight per volume of resulting mixture. Tween 20 is preferably added in the range of about 0.5% to about 2.0% and is most preferably added at 1.0%. The detergent treatment with 1% Tween 20 reduces enveloped viruses by >4 logs of clearance.

Another embodiment of the invention includes virus removal. Both enveloped and non-enveloped viruses are removed by filtration, preferably by nanofiltration, or any other filtration methods known in the art. In a preferred embodiment, the solution eluted from the ion exchange resin, which includes α-1 PI, is subjected to nanofiltration. Nanofiltration reduces both enveloped and non-enveloped viruses by >4 logs of clearance.

The methods of the current invention, therefore, preferably include two >4 logs of clearance steps for the removal of enveloped viruses and non-enveloped viruses. These viral clearance levels are greater than those obtained by known methods of manufacture of α-1 PI, which only include two virus clearance steps.

Practice of the invention will be understood more fully from the following examples, which are presented herein for illustration only and should not be construed as limiting the invention in any way.

EXAMPLE 1

In a preferred embodiment, the starting material is Cohn Fraction IV-1 paste, which is obtained by the Cohn-Oncley fractionation technique, well known to those of skill in the art. The preparation of an aqueous solution from the Fraction IV-1 paste is described below.

The IV-1 paste is dissolved in 24 volumes of Tris buffer (IV-1 paste weight in kg times 24) between 20 and 8° C. The solution is mixed for approximately 4.5 hrs. while maintaining the temperature between 2° and 8° C. After mixing, the pH of the solution is adjusted to between 9.25 and 9.5 using 1.0 M NaOH, which is added at a rate of 1.25 l/min. This solution is then mixed for 1 hr. and the pH readjusted, if necessary. The solution is then heated to 39° to 41° C. for 60 to 90 minutes to dissolve the Fraction IV-1 paste in the buffer solution.

EXAMPLE 2

Fraction IV-1, like other plasma fractions, contains various proteins, such as lipoproteins, imnnunoglobulins, globulin, metaprotein, etc. These proteins must be separated from the α-1 PI, but some will also bind to an ion exchange resin and thereby interfere with the purification of α-1 PI. Before adding the solution to an anion exchange resin, therefore, a portion of these contaminating proteins is preferably removed first. This example describes one purification step in the process for the removal of contaminating proteins.

The Cohn Fraction IV-1 dissolved in the Tris buffer solution, as described above, is again cooled to between 2° and 8° C. To this cooled solution is added NaCl to 0.11 M. To this solution is then added 11.5% PEG MW 3,350 (Carbowax®, Union Carbide, Danbury, Conn.; suspension weight in kg times 0.115). The pH of the solution is then adjusted to between 5.10 and 5.35 with 1.0 M glacial acetic acid. To this is added 2.5% of Hyflo Supercel® (Celite Corporation, Lompoc, Calif.) and the resulting solution is mixed for 10 min. A precipitate of contaminating proteins and viruses, including prion proteins, is formed. This precipitate is filtered through a filter press assembled with CP90 Cuno filter pads (Cuno, Meriden, Conn.) at NMT 20 psi. The press is rinsed with 11.5% PEG in a water buffer. The paste obtained by the filtration is discarded. The filtrate contains the α-1 PI in PEG. Alternatively, the precipitate may be centrifuged and then filtered.

EXAMPLE 3

In a preferred embodiment, the filtrate obtained from the PEG precipitation outlined in Example 2 above is subjected to viral inactivation in a non-ionic detergent. The pH of the filtrate from Example 2 above is adjusted to 7.0 to 7.2 with 1.0 M NaOH. To this solution is added Tween 20 to 1% (PEG filtrate weight in kg times 10.1 g/kg), and the pH adjusted to 6.9 to 7.1 with 1.0 M NaOH. This solution is held between 20° and 30° C. for 8–10 hrs. This treatment reduces enveloped viruses in the solution containing α-1 PI by >4 logs of clearance.

EXAMPLE 4

The solution containing α-1 PI in both PEG and Tween 20 is then passed through an anion exchange resin to further purify the α-1 PI and separate it from the PEG and Tween 20. Prior to addition of the solution to the anion exchange resin, the conductivity of the solution is adjusted so that the α-1 PI will bind to the anion exchange resin. The solution resulting from Example 3 above is diluted with water-for-injection (WFI) until the conductivity of the solution is reduced to a value between about 2.0 mS and about 6.0 mS at 25° C. Additional 1% Tween 20 may be included in the WFI to prolong the contact time of the solution with the detergent. The WFI may contain $Na_3PO_4$ (20 mM) at a pH of 6.5.

A Q Sepharose® (Amersham-Pharmacia Biotech, Upsala, Sweden) fast flow column is prepared and equilibrated with a 20 mM $Na_3PO_4$ solution at pH 6.5. The solution of α-1 PI in Tween 20 and PEG is then added to the column at a concentration of 8–12 mg of α-1 PI per milliliter of resin. The flow rate of the column is 125 cm/hr. The α-1 PI binds to the column, which is then washed with the 20 mM $Na_3PO_4$ solution at pH 6.5. The $Na_3PO_4$ buffer further removes contaminating proteins, such as albumin and transferrin, for example, from the column. An elution buffer of 0.025 M $Na_3PO_4$/0.1 M NaCl at pH 6.95–7.05 is passed through the column to remove the α-1 PI. The eluate, which contains the α-1 PI, is collected. Ceruloplasmin remains bound to the column until the NaCl strip.

The purification step, therefore, accomplishes four objectives: 1) separation of the α-1 PI from the PEG; 2) separation of the α-1 PI from the Tween 20; 3) purification of the α-1 PI; and 4) prolongation of the contact time of viruses in the solution with the Tween 20.

EXAMPLE 5

In a preferred embodiment of the invention, the aqueous solution containing α-1 PI is subjected to a further purification step following the Q Sepharose® chromatography outlined in Example 4 above. The further purification is accomplished by cation chromatography.

A Macro Prep High S® (BioRad Laboratories, Hercules, Calif.) column is prepared and equilibrated with a 20 mM $Na_3PO_4$/5 mM NaCl buffer at pH 5.45 to 5.54 until the column effluent consistently has a pH ≦5.60. Prior to adding the eluate containing α-1 PI obtained from the method of Example 4 above to the cation column, it may be concentrated by ultrafiltration and diafiltration. Dry $Na_3PO_4$ and NaCl are then added to the resulting concentrate to a final concentration of 20 mM $Na_3PO_4$ and 5 mM NaCl. The pH of the resulting solution is then adjusted to approximately 5.50 with 1.0 M glacial acetic acid. This solution is then applied to the column at a ratio of 5 mg contaminants (e.g., albumin and IgA) per milliliter of resin. The α-1 PI does not bind to the resin, while the contaminants do bind to the resin. The α-1 PI is chased through the column with a 20 mM $Na_3PO_4$/5 mM NaCl buffer at pH 5.45 to 5.54 to obtain a solution containing α-1 PI.

EXAMPLE 6

To further remove contaminating viruses, a filtration step is preferably included in methods of the invention. To the solution containing α-1 PI obtained by the process of Example 5 above is added NaCl to 0.75 M and the pH is adjusted to 7.0 with NaOH. The solution is then concentrated on a Viresolve 70® (Millipore, Bedford, Mass.) membrane using differential diafiltration with 0.75 M NaCl until the volume is reduced to 5%–20% of its original volume. Alpha-1 PI is washed through the Viresolve 70® membrane with 3–5 diafiltration volumes of 0.75 M NaCl.

Following the filtration, the resulting solution containing purified α-1 PI is concentrated by ultrafiltration and diafiltration. After diafiltration, the solution is concentrated, and the concentrated α-1 PI is formulated at about 55 mg of α-1 PI per milliliter of 20 mM $Na_3PO_4$ and 100 mM NaCl at pH 7.0. The formulated solution is sterile filtered. The resulting solution is lyophilized using methods known in the art.

The invention may be embodied in other specific forms without departing from the spirit or essential characteristics thereof. The foregoing examples are included by way of illustration only. Accordingly, the scope of the invention is limited only by the scope of the appended claims.

What is claimed is:

1. A method of purifying α-1 proteinase inhibitor from an aqueous solution containing α-1 proteinase inhibitor comprising:

(a) removing a portion of contaminating proteins from the aqueous solution by precipitation in order to obtain a purified solution containing α-1 proteinase inhibitor; then (b) passing said purified solution through an anion exchange resin so that α-1 proteinase inhibitor binds to said anion exchange resin; then (c) eluting α-1 proteinase inhibitor from said anion exchange resin to obtain an eluted solution containing α-1 proteinase inhibitor; then (d) passing the eluted solution through a cation exchange resin; then (e) collecting a flow-through from said cation exchange resin that contains α-1 proteinase inhibitor.

2. The method of claim 1, wherein said removing step comprises the steps of:

(a) precipitating said portion of contaminating proteins from said aqueous solution; and (b) separating said precipitated portion of contaminating proteins from said aqueous solution, thereby obtaining said purified solution containing α-1 proteinase inhibitor.

3. The method of claim 2, wherein said precipitating step comprises the steps of:
(a) adding a polyalkylene glycol to said aqueous solution; and
(b) adjusting the pH of said aqueous solution to from about 5.0 to about 6.0.

4. The method of claim 3, wherein said polyalkylene glycol is polyethylene glycol.

5. The method of claim 1, further comprising the step of, prior to said eluting step, washing said anion exchange resin with a buffer solution to remove a portion of contaminating proteins from said anion exchange resin so that α-1 proteinase inhibitor remains bound to said anion exchange resin.

6. The method of claim 1, further comprising a viral activation step.

7. The method of claim 6, wherein said viral inactivation step comprises the steps of:
(a) adding a detergent to said purified solution to obtain a mixture of detergent and purified solution; and
(b) adjusting the pH of said mixture to from about 6.5 to about 8.5.

8. The method of claim 7, wherein said detergent is a non-ionic detergent.

9. The method of claim 8, wherein said non-ionic detergent is Tween 20.

10. The method of claim 1, further comprising the step of removing viruses from said aqueous solution.

11. The method of claim 10, wherein said viral removal step comprises filtering said aqueous solution by nanofiltration.

12. The method of claim 1, further comprising a diluting step prior to passing said purified solution through said anion exchange resin.

13. The method of claim 12, wherein said diluting step comprises diluting said purified solution so that said purified solution has a conductivity of between about 2.0 mS and about 6.0 mS.

14. The method of claim 13, wherein said purified solution is diluted with water.

15. The method of claim 14, wherein the water contains sodium phosphate.

16. The method of claim 1, further comprising the step of adjusting a pH of said purified solution to between about 6.25 and about 7.25 prior to passing said purified solution through the anion exchange resin.

17. A method of purifying α-1 proteinase inhibitor from Cohn Fraction IV-I, comprising the steps of:
(a) removing a portion of contaminating proteins from said Cohn Fraction IV-I by precipitation in order to obtain a purified solution containing α-1 proteinase inhibitor; then
(b) passing said purified solution through an anion exchange resin so that α-1 proteinase inhibitor binds to said anion exchange resin; then
(c) eluting α-1 proteinase inhibitor from said anion exchange resin to obtain an eluted solution containing α-1 proteinase inhibitor; then
(d) passing the eluted solution through a cation exchange resin; then
(e) collecting a flow-through from said cation exchange resin that contains α-1 proteinase inhibitor.

18. The method of claim 17, wherein said removing step comprises the steps of:
(a) precipitating said portion of contaminating proteins from said Cohn Fraction IV-1; and
(b) separating said precipitated portion of contaminating proteins from said Cohn Fraction IV-1, thereby obtaining said purified solution containing α-1 proteinase inhibitor.

19. The method of claim 18, wherein said precipitating step comprises the steps of:
(a) adding a polyalkylene glycol to said Cohn Fraction IV-1; and
(b) adjusting the pH of said Cohn Fraction IV-1 to from about 5.0 to about 6.0.

20. The method of claim 19, wherein said polyalkylene glycol is polyethylene glycol.

21. The method of claim 17, further comprising the step of, prior to said eluting step, washing said anion exchange resin with a buffer solution to remove a portion of contaminating proteins from said anion exchange resin so that α-1 proteinase inhibitor remains bound to said anion exchange resin.

22. The method of claim 17, further comprising a viral activation step.

23. The method of claim 22, wherein said viral inactivation step comprises the steps of:
(a) adding a detergent to said purified solution to obtain a mixture of detergent and purified solution; and
(b) adjusting the pH of said mixture to from about 6.5 to about 8.5.

24. The method of claim 23, wherein said detergent is a non-ionic detergent.

25. The method of claim 24, wherein said non-ionic detergent is Tween 20.

26. The method of claim 17, further comprising the step of removing viruses from said aqueous solution.

27. The method of claim 26, wherein said viral removal step comprises filtering said aqueous solution by nanofiltration.

28. The method of claim 17, further comprising a diluting step prior to passing said purified solution through said anion exchange resin.

29. The method of claim 17, wherein said diluting step comprises diluting said purified solution so that said purified solution has a conductivity of between about 2.0 mS and about 6.0 mS.

30. The method of claim 29, wherein said purified solution is diluted with water.

31. The method of claim 30, wherein the water contains sodium phosphate.

32. The method of claim 17, further comprising the step of adjusting a pH of said purified solution to between about 6.25 and about 7.25 prior to passing said purified solution through the anion exchange resin.

33. The method of claim 17, wherein the Cohn Fraction IV-1 is suspended in an aqueous solution.

* * * * *